United States Patent [19]

Schoenwald et al.

[11] Patent Number: 5,104,887

[45] Date of Patent: Apr. 14, 1992

[54] TOPICAL OPHTHALMIC IMINO SUBSTITUTED 2-IMINO-3-METHYL-DELTA4-1,3,4-THIADIAZOLINE-5-SULFONAMIDES CARBONIC ANHYDRASE INHIBITORS

[75] Inventors: Ronald D. Schoenwald; Charles F. Barfknecht, both of Iowa City, Iowa

[73] Assignee: University of Iowa Research Foundation, Oakdale, Iowa

[21] Appl. No.: 751,309

[22] Filed: Aug. 28, 1991

Related U.S. Application Data

[63] Continuation-in-part of Ser. No. 410,982, Sep. 22, 1989, which is a continuation-in-part of Ser. No. 464,063, Feb. 4, 1983, Pat. No. 4,975,449.

[51] Int. Cl.$^5$ .............. C07D 277/62; C07D 277/68; C07D 277/76; A61K 31/425
[52] U.S. Cl. .................. 514/367; 514/913; 514/869; 514/363; 514/326; 536/4.1; 424/435
[58] Field of Search ............... 514/367, 326, 913, 869, 514/363; 536/4.1; 548/139; 424/435

[56] References Cited

U.S. PATENT DOCUMENTS

| | | | |
|---|---|---|---|
| 4,029,776 | 6/1977 | Cafruny et al. | 514/869 |
| 4,476,140 | 10/1984 | Sears et al. | 514/913 |
| 4,619,939 | 10/1986 | Maren | 514/913 |
| 4,746,745 | 5/1988 | Maren | 548/139 |
| 4,758,578 | 7/1988 | Tegeler et al. | 514/326 |
| 4,985,450 | 1/1991 | Tegeler et al. | 514/326 |
| 5,055,480 | 10/1991 | Pierce, Jr. | 514/363 |

OTHER PUBLICATIONS

DeBenedetti et al., "Chem Abstract"; vol. 108(15); p. 127395m; 1987.

Primary Examiner—Ronald W. Griffin
Assistant Examiner—Louise Leary
Attorney, Agent, or Firm—Zarley, McKee, Thomte, Voorhees & Sease

[57] ABSTRACT

High potency carbonic anhydrase inhibitors derived from methazolamide.

12 Claims, No Drawings

TOPICAL OPHTHALMIC IMINO SUBSTITUTED 2-IMINO-3-METHYL-DELTA4-1,3,4-THIADIAZOLINE-5-SULFONAMIDES CARBONIC ANHYDRASE INHIBITORS

CROSS-REFERENCE TO A RELATED APPLICATION

This application is a continuation-in-part of co-pending and commonly owned application Ser. No. 410,982, filed Sept. 22, 1989, entitled PRODRUGS OF CARBONIC ANHYDRASE INHIBITORS which itself is a continuation-in-part of copending and commonly owned application Serial No. 464,063 filed Feb. 4, 1983, now U. S. Pat. No. 4,975,449 and entitled TOPICAL TREATMENT FOR GLAUCOMA.

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive and some surgeons will use surgery only as a last resort.

Carbonic anhydrase inhibitors, prescribed orally, work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults, fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors (CAI), slow the formation of fluid by inhibiting a chemical reaction at the ciliary body. Along with their well-tested effectiveness comes nausea, tingling in fingers and toes, and other side effects. Oral drugs generally do not, however, cause side effects in the eye.

Certain topical drugs, while causing less systemic effects, on the other hand, can cause severe headaches and constrict the pupil, making the daytime appear dark.

In our grandparent application, analogs of 2-benzothiazole-sulfonamides are prepared as carbonic anhydrase inhibitors. While many of the compounds that are prepared are carbonic anhydrase active, in fact some have limited practical usage because the compounds are poorly soluble in water. This is not only true for certain carbonic anhydrase inhibitor active 2-benzothiazolesulfonamides, but it is also true for certain other carbonic anhydrase inhibitors such as methazolamide/acetazolamide analogs and dichlorphenamide analogs. Our parent application relates to prodrugs of these last three mentioned compounds.

Compounds which are carbonic anhydrase active inhibitors but have limited solubility in tears are, as a practical matter, of limited value in developing topical carbonic anhydrase inhibitors. Put another way, if the compound will not dissolve in the tears, its chances of penetrating the cornea to release the pharmacologically active carbonic anhydrase inhibitor are small, at best. Thus, it is important if one is developing effective carbonic anhydrase inhibitors which can be topically applied, that the compound be soluble in water and tears.

It is a primary objective of the present invention to provide carbonic anhydrase inhibitors with enhanced potency in comparison to methazolamide.

It is another objective of the present invention to prepare analogs of certain methazolamide carbonic anhydrase inhibitors. The drugs are soluble in tears, and can effectively penetrate the cornea and release the pharmacologically active carbonic anhydrase inhibitor by enzymatic and/or hydrolytic degradation of a chemical bond between a water soluble moiety and the carbonic anhydrase inhibitor.

The method and manner of accomplishing each of the above objectives as well as others will become apparent from the detailed description of the invention which follows hereinafter.

SUMMARY OF THE INVENTION

Compounds representing structural modification of the methazolamide molecule which represent substantially enhanced CAI potency over methazolamide. The compounds have physicochemical properties appropriate for topical opthalmic use.

DETAILED DESCRIPTION OF THE INVENTION

Inhibition of carbonic anhydrase is one mechanism of action by which the production of aqueous humor can be limited within the eye. If aqueous humor production can be limited, this in turn can be used to control ocular hypertension. Carbonic anhydrase inhibitors can be administered orally to reduce intraocular pressure (IOP), but this route of administration is associated with systemic side effects due to the large doses required to attain therapeutically useful levels in the eye. Topical administration of carbonic anhydrase inhibitors directly to the eye has the advantage of minimizing or eliminating systemic side effects due to the smaller doses required, and the more direct access the drug has to the organ. However, a carbonic anhydrase inhibitor may not produce optimum therapeutic effects, and may not be adequately absorbed or distributed to the active site, or may cause ocular irritation or local side effects as a result of changes in the carbonic anhydrase inhibitor molecule necessary to achieve water solubility. Thus, in preparing carbonic anhydrase inhibitors, one must constantly balance the activity, that is the effectiveness at inhibiting carbonic anhydrase, against the local or side effects that may be caused by changes necessary in the molecule in order to make it water soluble. For example, many carbonic anhydrase inhibitors that have been patented in the past achieve water solubility due to the presence of a tertiary amine which is protonated at physiological pH. In this situation, the less than optimal water solubility of the active carbonic anhydrase inhibitor is accompanied by enhanced lipophilic solubility which translates into greater penetration to the site of action. However, if optimal water solubility were obtained by protonation to the active carbonic anhydrase inhibitor, one would necessarily be faced with less lipophilic character and accordingly a decreased amount of drug reaching the site of action, due to the more difficult penetration of the cornea. The net result would be a less clinically effective agent.

In accordance with the present invention, it has been discovered how certain drugs prepared from analogs of methazolamide can be prepared and used as potent carbonic anhydrase inhibitors. The compounds are surprisingly more potent than methazolamide itself.

The carbonic anhydrase inhibitors of the methazolamide type described in my parent application were:

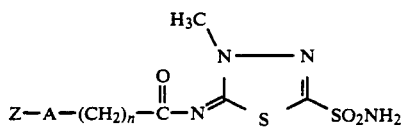

In the general formulas given for the hydroxymethazolamides, the "Z" represents a water soluble carrier and "A" is a moiety which is attached to the carbonic anhydrase inhibitor which allows it to still retain carbonic anhydrase inhibitory activity, but also form an enzymatically cleavable bond between A and Z. As used therein, "enzymatically cleavable bond" referred to a bond which can be cleaved after the compound is dropped onto the eye. The cleavage there described could be by enzymatic cleavage and/or hydrolytic cleavage. As a result, the water soluble compound was formed by covalently linking a pharmacologically active, but insufficiently water soluble, carbonic anhydrase inhibitor to a water soluble carrier, Z, through an enzymatically and/or hydrolytically degradable bond, "A". The water soluble prodrug dissolves in the tears, penetrates and degrades within the cornea to release the pharmacologically active carbonic anhydrase inhibitor which distributes and accumulates in the ciliary body, inhibits the enzyme carbonic anhydrase with a resulting decrease in the production of aqueous humor. Thus, intraocular pressure is reduced.

Key aspects of that invention were: First, synthesis of a molecule which inhibits carbonic anhydrase and has less than optimum water solubility itself, but which does contain a functional group which can be covalently linked through "A" to the water soluble carrier. Secondly, the linkage of the "carbonic anhydrase inhibitor-A" to a water soluble carrier by a covalent bond such as an ester, carbamate, carbonate, glycoside, etc. which can be degraded by enzymes present in the eye and/or hydrolyzed at physiological pH. Third, the water soluble carrier Z must attain its solubility due to the presence of two or more hydroxyl groups, and without the presence of groups which are ionized at physiological pH. Thus, the water soluble carrier was not to be a surface active agent or pharmacologically active itself.

Typical compounds which could be used as the water soluble carriers, Z, included monosaccharides such as D- and L-glucose, 6-carboxylic acid derivatives of monosaccharides such as D- and L-glucuronic acid, and D- and L-gluconic acid, and the like.

Suitable moieties represented by A include hydroxyalkoxy, preferably $C_1$ to $C_5$ alkyl, and most preferably alkoxyethoxy, simple hydroxy, hydroxy acetamido, and amine.

Where the water soluble non-ionizable carrier, Z, is a monosaccharide or a 6-carboxylic acid derivative of monosaccharides, it is preferred that A be hydroxyethoxy.

The linkage or covalent bond between Z and the carbonic anhydrase inhibitor ring system can be described as a covalent, degradable linkage between the active carbonic anhydrase inhibitor molecule and the water soluble carrier. This linkage can be an ester linkage, a glycosidic linkage, a carbonate linkage, a carbamate linkage, a thiocarbamate linkage, a urea linkage, a thiourea linkage, etc. Preferably, where Z is a monosaccharide the linkage is glycosidic and where Z is a 6-carboxylic acid derivative of a monosaccharide, the linkage is esteratic, i.e. through the carboxylic acid.

These compounds are water soluble, have greater than 0.25% solubility on a weight/volume basis without significant contributions from ionization at physiological pH. Also, the carbonic anhydrase inhibitor is a potent inhibitor of the enzyme carbonic anhydrase, and does have significant water solubility in comparison with the compound prior to attachment of the water soluble carrier Z. Also, the linkage between Z and A can be degraded by enzymes present in the eye such as acetylcholinesterase, serum cholinesterase, glycolase, etc., or can be degraded by hydrolysis/decomposition at physiological pH to release the active carbonic anhydrase inhibitor.

Examples of methazolamide or N-[5-(aminosulfonyl)-3-methyl-1,3,4-thiadiazol-2(3H)-ylidene]acetamide and its analogs which can be used are the following:
hydroxymethazolamide, N-[5-(aminosulfonyl)-3-methyl-1,3,4-thiadiazol-2(3H)-ylidene]hydroxyacetamide
and hydroxyethoxymethazolamide, N-[5-(aminosulfonyl)-3-methyl-1,3,4-thiadiazol-2(3H)-ylidene]hydroxyethoxyacetamide.

Other compounds modified from the parent molecule methazolamide and acetazolamide may also be prepared.

The compounds of the present invention can be generally described as Imino-substituted 2-Imino-3-methyl-delta$^4$-1,3,4-thiadiazoline-5-sulfonamides. Each of these compounds has a common structure similar to methazolamide. In particular, there are three general structures for the present compounds and those include the following:

STRUCTURE 1

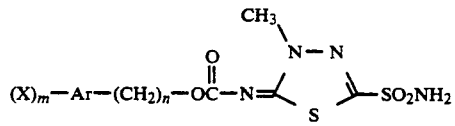

where
n=0,1,2,3,4,5
& X=hydrogen, hydroxyl, hydroxylmethyl, 2-hydroxyethyl, 2-hydroyethoxy
& Ar=phenyl, pyridyl, furanyl
% M=0.1,2,3,4

This structure covers 2-benzyloxycarbonylimio-3-methyl-delta-4-1,3,4-thiadiazoline-5-sulfonamide (example 2) which was synthesized/evaluated and 2-[4-pyridylmethyloxycarbony]imino- 3-methyl-delta4-1,3,4-thiadiazoline-5-sulfonamide and 2-[4-hydroxmethylbenzyloxycarbonyl]imino-3-methyl-delta4-1,3,4-thiadiazoline-5-sulfonamide]

The second group of methazolamide analogs have the following formula:

STRUCTURE 2

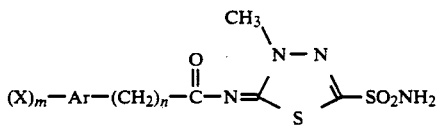

where
n=0,1,2,3,4,5
&X=hydrogen, hydroxyl, hydroxylmethyl, 2-hydroxyethyl, 2-hydroxyethoxy
& Ar=phenyl, pyridyl, furanyl
& M 0,1,2,3,4
This structure covers 2-[4-hydroxymethyl-phenylacetyl]-imino-3-methyl-delta$^4$-1,3,4-thiadiazoline-5-sulfonamide

STRUCTURE 3

The third group of methazolamide analogs have the following formula:

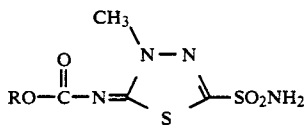

where R=$C_1$-$C_8$ alkyls This covers 2-ethoxycarbonylimino-3-methyl-delta$^4$-1,3,4-thiadiazoline-5-sulfonamide (example 2 below) which was synthesized/evaluated.

The following additional examples demonstrate the preparation of the methazolamide analogs, and their efficacy as topical carbonic anhydrase inhibitors.

EXAMPLE 1

Synthesis of 6-[1-glucopyranosyl)oxyethoxy]-2-benzothiazolesulfonamide

A solution of acetobromoglucose (4.93 g.; 12.0 mmole), 6-[2'-hydroxyethoxy]-2-benzothiazolesulfonamide (2.74 g.; 10.0 mmole), and 2,4,6-collidine (1.09 g.; 9.00 mmole) in dry tetrahydrofuran (50 mL) were added at −25° C. to a suspension of silver triflate (3.60 g.; 14.0 mmole) in dry tetrahydrofuran over a period of 30 minutes. The reaction mixture was stirred overnight at room temperature. Collidine (2 mL) was added and the mixture filtered through paper. The filtrate was washed with aqueous sodium thiosulfate solution, the organic layer separated, and evaporated to dryness at reduced pressure. The solid residue was chromatographed on a silica gel column (300 g.) and eluted with chloroform. The product fractions (UV light and charring positive) were combined and evaporated to dryness at reduced pressure.

The unpurified 6-[2'-(2",3",4",6'-tetra-0-acetyl-1-glucopyranosyl)oxyethoxy]-2-benzothiazolesulfonamide (3.02 g.; 5.00 mmole) was dissolved in anhydrous diethyl ether (100 mL) and combined with cold (0° C.) saturated methanolic ammonia (100 mL) and stirred overnight with the temperature rising to room temperature over a six hour period. The solution was evaporated to dryness at reduced pressure and chromatographed on a silica gel column (150 g.) and eluted with chloroform/methanol (9.1). The product fractions (UV light and charring positive) were combined and evaporated to dryness at reduced pressure, and lyophilized to yield 6-[1-glucopyranosyl)oxyethoxy]-2benzothiazolesulfonamide. The product conformed to accepted standards of purity and its structural assignment verified by standard spectroscopic methods (mass spec, $^{13}$C and $^1$H nuclear magnetic resonance).

EXAMPLE 2

Synthesis of 2-ethoxycarbonylimino-3-methyl-delt$^4$-1,3,4-thiadiazoline-5-sulfonamide Synthesis: A solution of 2-imino-3-methyl-delta$^4$-1,3,4- thiadiazoline-5sulfonamide [1.94 g; 10 mmole] in dry pyridine (50 ml) was cooled with ice. To the stirred solution ethyl chloroformate [1.30 g; 12 mmole] was added dropwise over a period of 15 minutes. The mixture was stirred at room temperature for 24 hours followed by the addition of 1 ml water and in vacuo evaporation. The water addition and in vacuo evaporation was repeated three time to give a crystalline mass which was recrystallized form ethyl acetatemethanol [5:1] to yield 1.62 g [61%]with melting point 189°–90° C.

EXAMPLE 3

Synthesis of 2-benzyloxycarbonylimino 3-methyl-delta$^4$-1,3,4-thiadiazoline-5-sulfonamide Synthesis: A solution of 2-imino-3-methyl-delta$^4$-1,3,4-thiadiazoline-5-sulfonamide (1.94 g; 10 mmole) in dry pyridine (50 ml) was cooled with ice. To the stirred solution benzyl chloroformate [2.05 g; 12 mmole] was added dropwise over a period of 15 minutes. The mixture was stirred at room temperature for 24 hours followed by the addition of 1 ml water and in vacuo evaporation. The water addition and in vacuo evaporation was repeated three time to give a crystalline mass which was recrystallized form ethyl acetatemethanol [5:1] to yield 1.22 g [37%] with melting point 180°–1° C.

EXAMPLE 4

Physico-chemical and Pharmacological

Measurements of Drugs from Examples 2 and 3

(a) Physicochemical Properties—Melting points were determined by differential scanning calorimetry (Perkin-Elmer 7 Series Thermal Analysis System) at a heating rate of 2 degrees/min. Solubilities were determined from saturated solutions using UV spectrophotometry.

Partition coefficients were obtained by equilibrating the test compound between octanol (saturated with buffer) and pH 7.65 1/15M Sorensen modified phosphate buffer at 37° (saturated with octanol). The concentration in the buffer phase was determined by UV spectrophotometry and the concentration in the octanol was determined by difference from the starting concentration. The PkA's were measured by titration of a weak acid with a dilute solution of NaOH.

The compounds from examples 2 and 3 were tested and compared to results obtained for methazolamide.

Result—The results in Table 1 below show that the compounds from examples 2 and 3 are more lipophilic and slightly less water soluble than methazolamide. The PkA values do not differ appreciably from methazolamide. (b) In Vitro Inhibition of Human Carbonic Anhydrase II—Inhibition of purified human erythrocyte carbonic anhydrase II (Sigma, St. Louis, Mo.) was determined using a pH stat assay (Mettler DL 21 Titrator). This assay measures hydrolysis of $CO_2$ by determining the rate at which a standard solution of NaOH is added to a buffered solution. A constant pH is maintained as $CO_2$ is added at a controlled rate. The detailed procedure is outlined below:

Enzyme: 40 mL of carbonic anhydrase II (0.1 mg/mL)
Titration: pH stat at pH 8.3
Buffer: tris hydrochloride pH 8.6 (0.02 M)
Titrant: sodium hydroxide (0.025 M 10 mL)
Gas: $CO_2/O_2$ (5/95) at a flow rate of about 75 mL/min
Reaction Temperature: 5 degrees centigrade
Equilibration Time: 5 minutes

TABLE 1

PHYSICOCHEMICAL AND PHARMACOLOGICAL ACTIVITY OF TOPICALLY ACTIVE DERIVATIVES OF METHAZOLAMIDE

|  | Ex. #2 | Ex. #3 | Methazolamide |
|---|---|---|---|
| Melting point (°C.) | 189-190 | 180-181 | 213-214 |
| Molecular weight | 266.3 | 328.4 | 236.3 |
| Solubility (mg/mL) | 2.70 | 0.11 | 3.53 |
| Distribution Coeff | 1.70 | 24.7 | 0.67 |
| pKa | 6.97 | 7.0 | 7.3 |
| $IC_{50}$ (nM) | 30.1 | 16.8 | 270. |
| Topical Activity | 9.9, 13.3 | 17%[b] | None[c] |
| % decline in IOP | and 23.6%[a] | | |

[a] Results are for 1% suspension, 2% suspension, and 2% in carbopol gel (3% carbomer), respectively
[b] Results are for 2% suspension
[c] Results are for 1 or 2% suspension Table 1 lists $IC_{50}$ values obtained for methazolamide, and drugs given in examples 2 and 3. $IC_{50}$ is the concentration that inhibits enzyme activity by 50%. The lower the value the more potent the drug. From the results it can be seen that one analog ($IC_{50}=30.1$) is approximately ten-fold more potent in activity when methazolamide ($IC_{50}=270$) and the other is even more potent ($IC_{50}=16.8$).

c. Topical Activity—The "IOP recovery rate assay" as by Vareilles and Lotti (Ophthal. Res., 13. 72–79, 1981) was used. In this assay 20% sodium chloride solution is infused into the marginal eary vein of New Zealand rabbits for 10 minutes at a rate of 1 mL/min. IOP was measured at 15, 25, 35, 45, 60, 75, 90, and 120 minutes. IOP is measured with an applanation pneumatonometer (Digilab Model D). Test drug was administered (see table 1) topically to the right eye 60 minutes before the start of the sodium chloride infusion. Control animals are given vehicle without drug.

The hypertonic sodium chloride solution causes a decline in IOP which then recovers at a rate dependent on the activity of carbonic anhydrase. IOP gradually returns to normal at a constant rate but more slowly if a carbonic anhydrase inhibitor is present at the active site in sufficient concentration. The return to normal IOP is measured from the positive linear slope which begins at about 30–45 minutes after starting the infusion.

Table 1 gives the results for both drugs from example 2 and 3 which are significantly more active topically when compared to methazolamide. Methazolamide when dosed topically and evaluated with this model shows no activity.

Other specific compounds fitting within the general description and known to be useful for carbonic anhydrase inhibitors include the following:

2-[4-pyridylmethyloxycarbony]imino-3-methyl-delta[4]-1,3,4-thiadiazoline-5-sulfonamide;

2-[4-hydroxymethylbenzyloxycarbonyl]imino-3-methyl-delta[4]-1,3,4-thiadiazoline-5-sulfonamide;

2-[4-hydroxymethylphenylacetyl]imino-3-methyl-delta[4]-1,3,4-thiadiazoline-5-sulfonamide;

The compounds prepared in these examples and above discussed and synthesized and evaluated demonstrate that these structural modification of the methazolamide molecule result in substantially enhanced potency over methazolamide.

What is claimed is:

1. Methazolamide analogs of the structure:

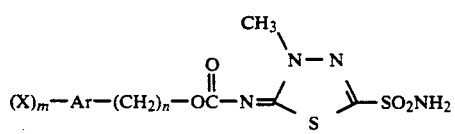

wherein n is an integer and is selected from 0, 1, 2, 3, 4, and 5, X is a moiety selected from the group of hydrogen, hydroxyl, hydroxymethyl, 2-hydroxyethyl, 2-hydroxyethoxy, Ar is a ring structure selected from phenyl, pyridyl, and furanyl, and m is a whole integer and is selected from 0, 1, 2, 3, and 4.

2. The compound of claim 1 which is 2-benzyloxcarbonylimino-3- methyl-delta[4]-1,3,4-thiadiazoline-5-sulfonamide.

3. The compound of claim 1 which is 2-[4-pyridylmethyloxy-carbony]imino-3-methyl-delta[4]-1,3,4-thiadiazoline-5-sulfonamide.

4. The compound of claim 1 which is 2-[4-hydroxymethylbenzyloxycarbonyl]imino-3-methyl-delta[4]-1,3,4-thiadiazoline-5sulfonamide].

5. An analog of methazolamide of the following formula:

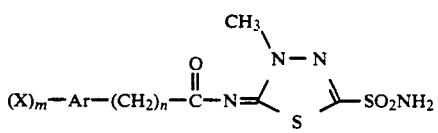

where n is a whole integer and is selected from 0, 1, 2, 3, 4, and 5, X is a moiety selected from the group consisting of hydrogen, hydroxyl, hydroxymethyl, 2-hydroxyethyl, and 2-hydroxyethoxy, Ar is a ring structure selected from the group consisting of phenyl, pyridyl, and furanyl, and M is a whole integer selected from 0, 1, 2, 3, and 4.

6. The compound of claim 5 which is 2-[4-hydroxymethylphenylacetyl]-imino-3-methyl-delta[4]-1,3,4-thiadiazoline-5-sulfonamide.

7. A methazolamide analog of the following formula:

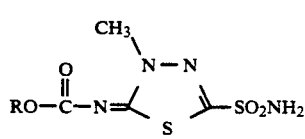

wherein R is a $C_1$-$C_8$ alkyl.

8. The compound of claim 7 wherein R is a $C_1$–$C_4$ alkyl.

9. The compound of claim 7 which is 2-ethoxycarbonylimino-3-methyl-delta 4-1,3,4-thiadiazoline-5-sulfonamide.

10. The compound of claim 7 which is 2-[4-pyridylmethyloxycarbonyl]imino-3-methyl-delta$^4$-1,3,4-thiadiazoline-5-sulfonamide.

11. The compound of claim 7 which is 2-[4-hydroxymethylbenzyloxycarbonyl]imino-3-methyl-delta$^4$-1,3,4-thiadiazoline-5-sulfonamide.

12. The compound of claim 7 which is 2-[4-hydroxymethylphenylacetyl]imino-3-methyl-delta$^4$-1,3,4-thiadiazoline-5-sulfonamide.

* * * * *